(12) United States Patent
Mathies et al.

(10) Patent No.: US 6,177,247 B1
(45) Date of Patent: *Jan. 23, 2001

(54) DETECTION METHODS USING PROBES LABELED WITH ENERGY TRANSFER COUPLED DYES FOR DNA FRAGMENT ANALYSIS

(75) Inventors: Richard Mathies, El Cerrito; Alexander Glazer, Orinda; Jingyue Ju, Berkeley, all of CA (US)

(73) Assignee: The Regents of the University of California, Oakland, CA (US)

( * ) Notice: Under 35 U.S.C. 154(b), the term of this patent shall be extended for 0 days.

This patent is subject to a terminal disclaimer.

(21) Appl. No.: 09/201,078

(22) Filed: Nov. 30, 1998

Related U.S. Application Data

(63) Continuation of application No. 08/790,813, filed on Jan. 30, 1997, now Pat. No. 5,869,255, which is a continuation-in-part of application No. 08/411,573, filed on Mar. 27, 1995, now abandoned, which is a continuation-in-part of application No. 08/189,924, filed on Feb. 1, 1994, now Pat. No. 5,654,419.

(51) Int. Cl.[7] ................................................. C12Q 1/68
(52) U.S. Cl. ............................ 435/6; 435/5; 435/7.1; 435/7.2; 536/25.4
(58) Field of Search ...................... 435/5, 6, 7.1, 7.2; 536/23.1, 25.4

(56) References Cited

U.S. PATENT DOCUMENTS

| | | | |
|---|---|---|---|
| 4,996,143 | 2/1991 | Heller et al. | 435/6 |
| 5,210,015 | 5/1993 | Gelfand et al. | 435/6 |
| 5,217,866 | * 6/1993 | Summerton et al. | 435/6 |
| 5,314,809 | 5/1994 | Erlich et al. | 435/91.2 |
| 5,326,692 | 7/1994 | Brinkley et al. | 435/6 |
| 5,401,847 | 3/1995 | Glazer et al. | 546/107 |
| 5,573,909 | 11/1996 | Singer et al. | 435/6 |
| 5,646,264 | 7/1997 | Glazer et al. | 536/25.32 |
| 5,728,529 | * 3/1998 | Metzker et al. | 435/6 |
| 5,869,255 | * 2/1999 | Mathies et al. | 435/6 |

FOREIGN PATENT DOCUMENTS

| | | |
|---|---|---|
| 5-60698 | 9/1991 | (JP) . |
| WO 90/03446 | 4/1990 | (WO) . |
| WO 93/06482 | 4/1993 | (WO) . |
| WO 93/10267 | 5/1993 | (WO) . |

OTHER PUBLICATIONS

S. Agrawal and P.C. Zamecnik, *Nucleic Acids Research* (Aug. 1990) 18(18): 5419–5423.
U. Asseline et al., *EMBO Journal* (Jan. 1984) 3(4): 795–800.
D. Bergstrom, et al., *Synlett: Accounts and Rapid Communications in Synthetic Organic Chemistry* (Mar. 1992) 3: 179–188.

(List continued on next page.)

*Primary Examiner*—Ardin H. Marschel
(74) *Attorney, Agent, or Firm*—Townsend and Townsend and Crew LLP

(57) ABSTRACT

Compositions are provided comprising sets of fluorescent labeled oligonucleotides carrying pairs of donor and acceptor dye molecules, designed for efficient excitation of the donors at a single wavelength and emission from the acceptor in each of the pairs at different wavelengths. The different molecules having different donor-acceptor pairs can be modified to have substantially the same mobility and enhanced emission intensities under separation conditions, by varying the distance between the donor and acceptor in a given pair. Particularly, the fluorescent compositions find use as labels in analyzing double stranded and single stranded nucleic acid fragments using capillary electrophoresis.

45 Claims, 7 Drawing Sheets

(3 of 7 Drawing Sheet(s) Filed in Color)

OTHER PUBLICATIONS

S.C. Benson et al., *Nucleic Acids Research* (Nov. 1993) 21(24): 5720–5726, 5727–5735.

J. Brumbaugh et al., *Proc. Natl. Acad. Sci. USA* (Aug. 1998) 85: 5610–5614.

R.A. Cardullo et al. *Proc. Natl. Acad. Sci. USA* (Dec. 1998) 85: 8790–8794.

R.M. Clegg, *Methods in Enzymology* (1992) 211: 353–389.

J.P. Cooper and P.J. Hagerman, *Biochemistry* (Jul. 1990) 29: 9261–9268.

J.M. Drake et al. *Science* (Mar. 1991) 251: 1574–1579.

R.P. Haugland., Small Business Innovation Research Program, Phase I Grant Application, submitted Dec. 13, 1985, and associated work.

R.P. Haugland, "Fluorescence–Detected DNA Sequencing, Final Technical Report," Grant No. DE–FG06–88ER60684, Sep. 29, 1990.

M.J. Heller et al. *Federation Proceedings* (Jun. 1987) 46(6): Abstract.

H–C. Kang et al., "Human Genome 1989–90 Program Report" (Mar. 1990) p. 55.

L.G. Lee et al. *Nucleic Acids Research* (Apr. 1992) 20(10): 2471–2483.

L.G. Lee et al. *Nucleic Acids Research* (Jun. 1993) 21(16): 3761–3766.

P.S. Nelson et al. *Nucleic Acids Research* (Aug. 1989) 17(18): 7187–7194.

H. Ozaki and L.W. McLaughlin, *Nucleic Acids Research* (Sep. 1992) 20(19): 5205–5214.

S. Sixou et al., *Nucleic Acids Research* (Dec. 1993) 22(4): 662–668.

L. Stryer and R.P. Haugland, *Proc. N.A.S.* (1967) 38:719–726.

R.P. Haugland, Small Business Innovation Research Program, Phase II Grant Application, proposed period Mar. 1, 1988–Feb. 28, 1991.

R.P. Haugland, "Fluorescence–Detected DNA Sequencing," Dept. of Energy, Research Abstracts for 1988.

R.P. Haugland, U.S. Dept. of Energy, Grant Application, dated Oct. 31, 1997.

* cited by examiner

DETECTION METHODS USING PROBES LABELED WITH ENERGY TRANSFER COUPLED DYES FOR DNA FRAGMENT ANALYSIS

CROSS-REFERENCE TO RELATED APPLICATION

This application is a continuation of application Ser. No. 08/790,813, filed Jan. 30, 1997, now U.S. Pat. No. 5,869,255 which is a continuation-in-part of application Ser. No. 08/411,573, filed Mar. 27, 1995, now abandoned; which is a continuation-in-part of application Ser. No. 08/189,924, filed Feb. 1, 1994, now U.S. Pat. No. 5,654,419. The disclosures of all applications and patents cited in this paragraph are incorporated herein by reference.

TECHNICAL FIELD

The field of this invention is fluorescent tags and their use as exemplified with DNA fragment analysis.

BACKGROUND

There is an increasing demand to be able to identify and quantify components of mixtures. The greater the complexity of the mixture, the greater the interest in being able to simultaneously detect a plurality of the components present. As illustrative of this situation is DNA sequencing and DNA fragment analysis, where it is desirable to efficiently excite from one to four or more fluorescently tagged components with a laser source at a single wavelength, while providing for fluorescent signal emission at a plurality of distinctive wavelengths. In this situation, the different labels should not adversely affect the electrophoretic mobility of DNA fragments to which they are attached.

Currently, there are four methods used for automated DNA sequencing: (1) the DNA fragments are labeled with one fluorophore and then the fragments run in adjacent sequencing lanes (Ansorge et al., *Nucleic Acids Res.* 15, 4593–4602 (1987); (2) the DNA fragments are labeled with four different fluorophores and all the fragments are electrophoretically separated and detected in a single lane (Smith et al., *Nature* 321, 674–679 (1986); (3) each of the dideoxynucleosides in the termination reaction is labeled with a different fluorophore and the four sets of fragments are run in the same lane (Prober et al., *Science* 238, 336–341 (1987); or (4) the sets of DNA fragments are labeled with two different fluorophores and the DNA sequences coded with the dye ratios (Huang et al., *Anal. Chem.* 64, 2149–2154 (1992). For fluorescence based PCR DNA fragments analysis, primers labeled with different fluorescent dyes were employed thereby permitting multiple target analysis (Andy et al. (1995) Biotechniques, 18, 116–121).

All of these techniques have significant deficiencies. Method 1 has the potential problems of lane-to-lane variations in mobility, as well as a low throughput. Methods 2, 3 and 4 as well as the multiple color PCR method require that the four dyes be well excited by one laser source and that they have distinctly different emission spectra. In practice, it is very difficult to find two or more dyes that can be efficiently excited with a single laser and that emit well separated fluorescent signals.

As one selects dyes with distinctive red-shifted emission spectra, their absorption maxima will also move to the red and all the dyes can no longer be efficiently excited by the same laser source. Also, as more different dyes are selected, it becomes more difficult to select all the dyes such that they cause the same mobility shift of the labeled molecules.

It is therefore of substantial interest that improved methods be provided which allow for multiplexing of samples, so that a plurality of components can be determined in the same system and in a single run. It is also desirable for each label to have strong absorption at a common wavelength, to have a high quantum yield for fluorescence, to have a large Stokes shift of the emission, that the various emissions be distinctive, and that the labels introduce the same mobility shift. It is difficult to accomplish these conflicting goals by simply labeling the molecules with a single dye.

SUMMARY OF THE INVENTION

The subject invention provides compositions and methods for analyzing a mixture using a plurality of fluorescent labels. To generate the labels, pairs or families of fluorophores are bound to a backbone, particularly a nucleic acid backbone, where one of the members of the families is excited at about the same wavelength. By exploiting the phenomenon of energy transfer, the other members of each of the families emit at detectably different wavelengths. The range of distances between donor and acceptor chromophores is chosen to ensure efficient energy transfer. Furthermore, labels used conjointly are selected to have approximately the same mobility shift in a separation system, where one of the labels may have two molecules of the same fluorescer, so as to provide the fluorescence emission of the single fluorescer, but the same mobility shift as the different donor-acceptor chromophore labels. This is achieved by changing the mobility shift of the labeled entity, by varying the distance between the two or more members of the family of fluorophores and by choosing labels with the same mobility. The subject invention finds particular application in DNA sequencing and DNA fragment sizing, where the fluorophores may be attached to universal or other primers and different fluorophore combinations used for the different dideoxynucleosides. Kits of combinations of labels are also provided.

BRIEF DESCRIPTION OF THE DRAWINGS

The file of this patent contains at least one drawing executed in color. Copies of this patent with color drawings will be provided by the Patent and Trademark Office upon request and payment of the necessary fee.

SCHEME 1. Structures of the four energy transfer (ET) primers (SEQ ID NOs: 1–4) and a representative synthetic scheme for the preparation of F6R (SEQ ID NOs: 5 and 6). The fluorescent primers are labeled with a common fluorescein donor (F) at the 5' end and either a second fluorescein or a rhodamine (R) acceptor at the indicated locations of a modified T in the sequence. The number of nucleotides between the two fluorophores is indicated in the primer designation.

DESCRIPTION OF SPECIFIC EMBODIMENTS

Figure 1:
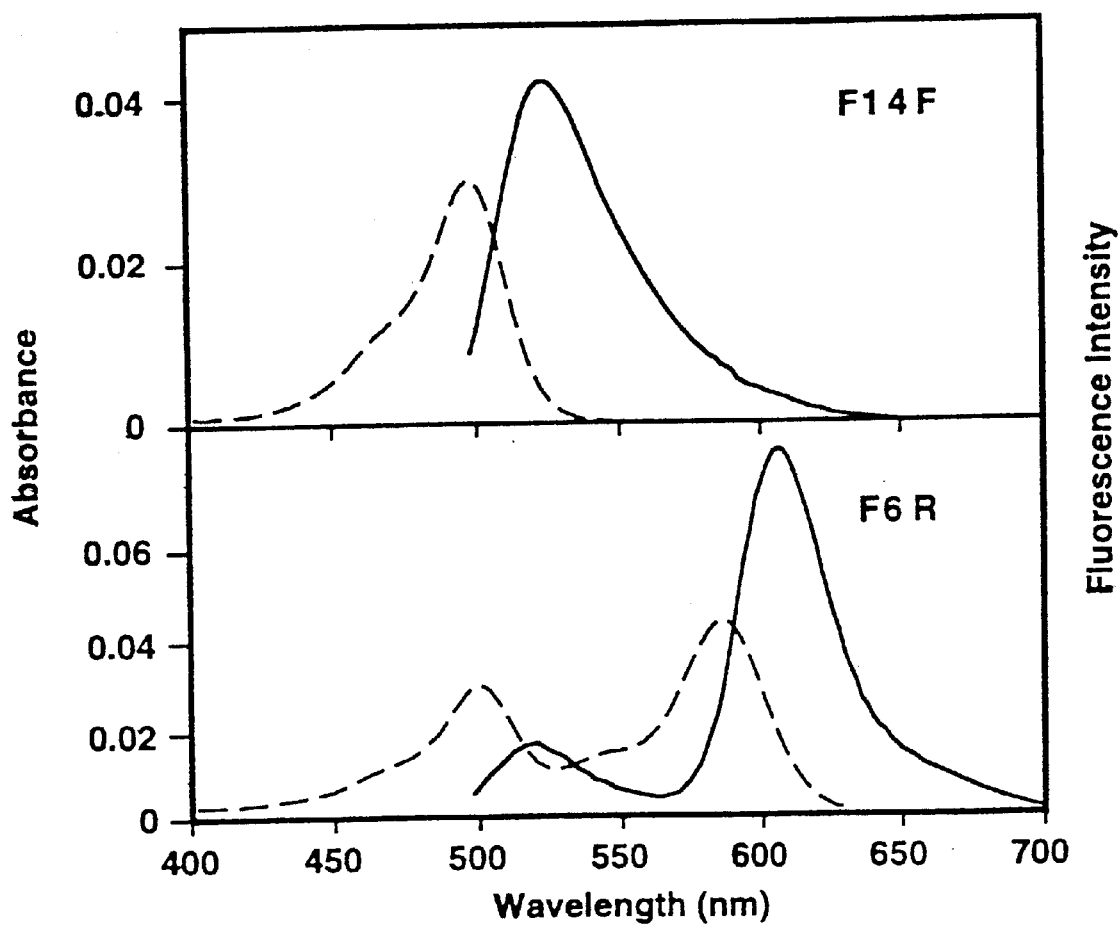
FIG. 1 shows the absorption ( - - - ) and fluorescence emission (_____) spectra of the fluorescently labeled THO1 primers F14F and F6R measured in 1×TBE. F14F exhibits strong absorption at ~488 nm and intense fluorescence emission with a maximum at 525 nm. F6R also exhibits intense absorption at ~488 nm but the maximum emission is shifted out to ~600 nm.

Novel fluorescent labels, combinations of fluorescent labels, and their use in separation systems involving the separation of a plurality of components are provided. Particularly, the fluorescent labels comprise pairs of fluorophores, which with one exception where the fluorophores are the same, involve different fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

The donor fluorophores in the different families of fluorophores may be the same or different, but will be able to be excited efficiently by a single light source of narrow bandwidth, particularly a laser source. The donor fluorophores will have significant absorption, usually at least about 10%, preferably at least about 20% of the absorption maxima within 20 nm of each other, usually within 10 nm, more usually within 5 nm, of each other. The emitting or accepting fluorophores will be selected to be able to receive the energy from donor fluorophores and emit light, which will be distinctive and detectably different. Therefore, one will be able to distinguish between the components of the mixture to which the different labels have been bound. Usually the labels will emit at emission maxima separated by at least 10 nm, preferably at least 15 nm, and more preferably at least 20 nm.

Usually the donor fluorophores will absorb in the range of about 350–800 nm, more usually in the range of about 350–600 nm or 500–750 nm, while the acceptor fluorophores will emit light in the range of about 450–1000 nm, usually in the range of about 450–800 nm. As will be discussed subsequently, one may have more than a pair of absorbing molecules, so that one may have 3 or more molecules, where energy is transferred from one molecule to the next at higher wavelengths, to greatly increase the difference in wavelength between absorption and observed emission.

The two fluorophores will be joined by a backbone or chain, usually a polymeric chain, where the distance between the two fluorophores may be varied. The physics behind the design of the labels is that the transfer of the optical excitation from the donor to the acceptor depends on $1/R^6$, where R is the distance between the two fluorophores. Thus, the distance must be chosen to provide efficient energy transfer from the donor to the acceptor through the well-known Foerster mechanism. Thus, the distance between the two fluorophores as determined by the number of atoms in the chain separating the two fluorophores can be varied in accordance with the nature of the chain. Various chains or backbones may be employed, such as nucleic acids, both DNA and RNA, modified nucleic acids, e.g. where oxygens may be substituted by sulfur, carbon, or nitrogen, phosphates substituted by sulfate or carboxylate, etc., polypeptides, polysaccharides, various groups which may be added stepwise, such as di-functional groups, e.g. haloamines, or the like. of particular interest is nucleic acid, particularly DNA and RNA as the backbone, where the bases may be naturally occurring or synthetic, particularly naturally occurring. The fluorophores may be substituted as appropriate by appropriate functionalization of the various building blocks, where the fluorophore may be present on the building block during the formation of the label, or may be added subsequently, as appropriate. Various conventional chemistries may be employed to ensure that the appropriate spacing between the two fluorophores is obtained. In the case of the label having two molecules of the same fluorophore, the spacing will be selected to have the same mobility as a label having two molecules having different fluorophores. The label with the same fluorophores need not have efficient energy exchange, so that there is substantial flexibility in the separation of the same fluorophores to achieve the desired mobility. However, the two fluorophores should be spaced to avoid self quenching, so that the two fluorophores will usually be spaced more than about 2 nucleotides apart.

The molecular weights of the labels (fluorophores plus the backbone to which they are linked) will generally be at least about 250 Dal and not more than about 20,000 Dal, usually not more than about 10,000 Dal. The molecular weight of the fluorophore will generally be in the range of about 250 to 1,000 Dal, where the molecular weights of the acceptor-donor pairs on different labels to be used together will usually not differ by more than about 20%. The fluorophores may be bound internal to the chain, at the termini, or one at one terminus and another at an internal site. The fluorophores may be selected so as to be from a similar chemical family, such as cyanine dyes, xanthenes or the like. Thus, one could have the donors from the same chemical family, each donor-acceptor pair from the same chemical family or each acceptor from the same family or the cross combination of the family.

The subject labels find particular application in various separation techniques, such as electrophoresis, chromatography, or the like, where one wishes to have optimized spectroscopic properties, high sensitivity and comparable influence of the labels on the migratory aptitude or nobility of the components being analyzed. Of particular interest is electrophoresis, such as gel, capillary, etc. Among chromatographic techniques are HPLC, affinity chromatography, thin layer chromatography, paper chromatography, and the like.

It is found that the spacing between the two fluorophores will affect the mobility of the label. Therefore, one can use combinations of the same dye pair and different dye pairs and by varying the distance between the dye pairs, within a range which still permits good energy transfer for the different dye pairs, provide for substantially constant mobility for the labels. The mobility is generally not linearly related to the specific spacing, so that one will empirically determine the effect of the spacing on the mobility of a particular label. However, because of the flexibility in the spacing of the fluorophores in the labels, by synthesizing a few different labels with different spacings and different dye pairs, one can now provide for a family of fluorescent labels, which share a common excitation, that have strong and distinctive emission and a substantially common mobility. Usually, the mobility will differ by not more than about 20% of each other, preferably not more than about 10% of each other, and more preferably within about 5% of each other, when used in a particular separation. The mobility may usually be determined by carrying out the separation of the labels by themselves or the labels bound to a common molecule which is relevant to the particular separation, e.g. a nucleic acid molecule of the appropriate size, where one is interested in sequencing or sizing.

A wide variety of fluorescent dyes may find application. These dyes will fall into various classes, where combinations of dyes may be used within the same class or between different classes. Included among the classes are dyes, such as the xanthene dyes, e.g. fluoresceins and rhodamines, coumarins, e.g. umbelliferone, benzimide dyes, e.g. Hoechst 33258, phenanthridine dyes, e.g. Texas Red, and ethidium dyes, acridine dyes, cyanine dyes, such as thiazole orange, thiazole blue, Cy 5, and Cyfr, carbazole dyes, phenoxazine dyes, porphyrin dyes, quinoline dyes, or the like. Thus, the dyes may absorb in the ultraviolet, visible or infra-red ranges. For the most part, the fluorescent molecules will have a molecular weight of less than about 2 kDal, generally less than about 1.5 kDal.

The energy donor should have a strong molar absorbance coefficient at the desired excitation wavelength, desirably greater than about $10^4$, preferably greater than about $10^5$ cm$^{-1}$M$^{-1}$. The absorption maximum of the donor and the emission maximum of the acceptor (fluorescer) will be separated by at least 15 nm or greater. The spectral overlap integral between the emission spectrum of the donor chromophore and the absorption spectrum of the acceptor chromophore and the distance between the chromophores will be such that the efficiency of energy transfer from donor to acceptor will range from 20% to 100%. Separation of the donor and acceptor based on number of atoms in the chain will vary depending on the nature of the backbone, whether rigid or flexible, involving ring structures or non-cyclic structures or the like. Generally the number of atoms in the chain (the atoms in the ring structures will be counted as the lowest number of atoms around one side of the ring for inclusion in the chain) will be below about 200, usually below about 150 atoms, preferably below about 100, where the nature of the backbone will influence the efficiency of energy transfer between donor and acceptor.

While for the most part, pairs of fluorophores will be used, there can be situations where up to four different, usually not more than three different, fluorophores bound to the same backbone may find use. By using more fluorophores, one may greatly extend the Stokes shift, so that one may excite in the visible wavelength range and emit in the infra-red wavelength range, usually below about 1000 nm, more usually below about 900 nm. Detecting light in the infra-red wavelength range has many advantages, since it will not be subject to interference from Raman and Rayleigh light resulting from the excitation light. In order to maintain the mobility constant, one may use the same number of fluorophores on the labels, having a multiplicity of the same fluorophore to match the number of fluorophores on Labels having different fluorophores for the large Stokes shift.

The subject invention finds particular application with nucleic acid chains, where the nucleic acid chains find use as primers in sequencing, the polymerase chain reaction, particularly for sizing, or other system where primers are employed for nucleic acid extension or ligation and one wishes to distinguish between various components of the mixture as related to the particular labels. For example, in sequencing, universal primers may be employed, where a different pair of fluorophores are used for each of the different dideoxynucleosides used for the extension during sequencing.

A large number of nucleosides are available, which are functionalized, and may be used in the synthesis of a polynucleotide. By synthesizing the subject nucleic acid labels, one can define the specific sites at which the fluorophores are present. Commercially available synthesizers may be employed in accordance with conventional ways, so that any sequence can be achieved, with the pair of fluorophores having the appropriate spacing.

Where different primers have been used in PCR, each of the primers may be labeled in accordance with the subject invention, so that one can readily detect the presence of the target sequence complementary to each of the different primers. Other applications which may find use include identifying isozymes, using specific antibodies, identifying lectins using different polysaccharides, and the like.

Also, of great interest is the use of the subject labels with rapid sizing of alleles, as exemplified by short tandem repeat (STR) alleles, or other sequences where one wishes to detect small base or base pair differences, such as small differences of as few as a single base or base pair. By using the subject labels in conjunction with capillary electrophoresis, particularly capillary array electrophoresis, and employing an intercalating agent in the buffer, separations differing by one base may be achieved. The method can be used with dsDNA, particularly dsDNA obtained using the polymerase chain reaction or the ligase chain reaction, where the subject labels may be used as primers. One or both of the primers for the amplification may be labels, where the fluorophore pairs may be the same or different, depending on the needs of the separation. The intercalating agents may be fluorescent or non-fluorescent, such as thiazole orange, 9-aminoacridine, ethidium bromide, and the like, but for the specific example give here they are preferably non-fluorescent. Concentrations will generally be in the range of 0.1 to 10 $\mu$M. Conventional conditions may be used for the capillary electrophoresis, using a polyacrylamide wall coating and, for example, using hydroxyethylcellulose at from about 0.5 to 1% in an appropriate running buffer. Voltages may vary from about 50 to 150V/cm or larger. The amount of DNA will generally be in the range of about 1 pg/$\mu$l to 1 ng/$\mu$l, although greater or lesser amounts may be used. obviously, such method can also be used for single strand (ss) DNA fragment analysis to detect the labelled ssDNA fragments by virtue of their fluorescence, using linear polyacrylamide or the like in CE, which permits single base resolution.

Kits are provided having combinations of labels, usually at least 2. Each of the labels will have the acceptor-donor pair, usually with comparable backbones, where the labels will be separated along the backbone to give comparable mobility in the separation method to be used. Each of the labels in a group to be used together will absorb at about the same wavelength and emit at different wavelengths, where one or more of the labels may conveniently have the same fluorescer as the donor and the acceptor. In each kit there will usually be at least one label with different fluorescers as the donor and acceptor. In order to be able to use the same excitation source, the labels having the same fluorescer for the pair, should have substantially overlapping absorption spectra, and different emission spectra. Therefore, the number of different labels capable of being used in a set, where the individual label has a common chromophore will be relatively limited. Each of the labels in the group will have about the same effect on mobility in the separation method, as a result of the variation in placement of the different fluorophores along the backbone.

The kits will generally have up to about 6, usually about up to about 4 different labels which are matching in mobility, but may have 2 or more sets of matching labels, having 2–6 different labels.

Of particular interest are labels comprising a nucleic acid backbone, where the labels will generally have at least about 10 nucleotides and not more than about 50 nucleotides, usually not more than about 30 nucleotides. The labels may be present on the nucleotides which hybridize to the complementary sequence or may be separated from those nucleotides. The fluorophores will usually be joined to the nucleotide by a convenient linking arm of from about 2 to 20, usually 4 to 16 atoms in the chain. The chain may have a plurality of functionalities, particularly non-oxo-carbonyl, more particularly ester and amide, amino, oxy, and the like. The chain may be aliphatic, alicyclic, aromatic, heterocyclic, or combinations thereof, usually comprising carbon, nitrogen, oxygen, sulfur, or the like in the chain.

The fluorophores will usually be separated by not more than about 20 nucleotides, usually not more than about 15 nucleotides.

The entire nucleic acid sequence may be complementary to the 5' primer sequence or may be complementary only to the 3' portion of the sequence or to any portion within the target sequence. Usually, there will be at least about 4 nucleotides, more usually at least about 5 nucleotides which are complementary to the sequence to be copied. For PCR reactions the primers are combined with the sequence to be amplified along with Taq polymerase and dNTPs. After amplification, the DNA may be isolated and transferred to a gel or capillary for separation.

The kits which are employed will have at least two of the subject labels, which will be matched by having substantially the same absorption for the donor molecule, distinct emission spectra and substantially the same mobility. Generally for single stranded nucleic acids, the separation will be from about 2–20, more usually 2–15, preferably about 2–14 nucleosides between fluorophores.

The following examples are offered by way of illustration and not by way of limitation.

Rapid Sizing of Short Tandem Repeat (STR) Alleles Using Energy-Transfer (ET) Fluorescent Primers and Capillary Array Electrophoresis Experimental Instrumentation. Capillary array electrophoresis separations were detected with the laser-excited, confocal-fluorescence scanner as previously described by Huang et al.(Huang et al. (1992) Anal. Chem. 1992, 64, 967–972. and Anal. Chem. 1992, 64, 2149–2154). Briefly, excitation light at 488 nm from an argon ion laser is reflected by a long-pass dichroic beam splitter, passed through a 32×, N.A. 0.4 microscope objective, and brought to a 10 $\mu$m diameter focus within the 75 $\mu$m i.d. capillaries in the capillary array. The fluorescence is collected by the objective, passed back through the first beam splitter to a second dichroic beam splitter that separates the red ($\lambda$>565 nm) and green ($\lambda$<565 nm) detection channels. The emission is then focused on 400 $\mu$m diameter confocal pinholes, spectrally filtered by a 590 nm long-pass filter (red channel) or a 20 nm band-pass filter centered at 520 nm (green channel), followed by photomultiplier detection. The output is preamplified, filtered, digitized, and then stored in an IBM PS/2 computer. A computer-controlled stage is used to translate the capillary array past the optical system at 20 mm/s. The fluorescence is sampled unidirectionally at 1500 Hz/channel. The scanner construction and operation have recently been described in detail (Mathies et al. (1994), Rev. Sci. Instrum. 65, 807–812). Postacquisition image processing was performed with the programs IPLab, KaleidaGraph and Canvas.

Capillary Electrophoresis. Polyacrylamide-coated, fused-silica capillaries were prepared using a modification of the procedure described by Hjerten et al. ((1985), J. Chromatogr. 347, 191–198). A 2–3 mm wide detection window was produced by burning off the polyimide coating with a hot wire followed by cleaning the external surface with ethanol. The detection window was placed 25 cm from the injection ends of the 75 $\mu$m i.d., 350 Am o.d., 50 cm long fused silica capillaries (Polymicro Technologies, Phoenix, Ariz.). The inner walls of the capillaries were incubated with 1 N NaOH for 30 min at room temperature, followed by rinsing with deionized water. The capillaries were then treated overnight at room temperature with $\gamma$-methacryloxypropyl-trimethoxysilane (1: 250 dilution with $H_2O$ adjusted to pH 3.5 with acetic acid) to derivatize the walls for acrylamide binding. Freshly-made 4% T acrylamide solution in 1/2×TBE buffer (45 mM tris, 45 mM boric acid, 1 mM EDTA, pH 8.3) was filtered with a 0.2 $\mu$m syringe filter and degassed under vacuum for 30 min. One $\mu$l TEMED (tetramethylethylenediamine) and 10 $\mu$l of 10% APS (ammonium persulfate) solution were added to 1 ml of gel solution. The solution was immediately forced into the capillary with a 100-$\mu$l syringe. After 30 min, the acrylamide solution was flushed out with deionized water and capillaries were filled with buffer consisting of hydroxyethyl cellulose (HEC) ($M_n$=438,000, Aqualon Co. Hopewell, Va.) dissolved in 1/2×TBE. The separation buffer was prepared by adding 0.8 g HEC to 100 ml 1/2×TBE and dissolved by stirring overnight at room temperature. The HEC buffer was degassed under vacuum for 30 min, centrifuged for 20 min on a tabletop centrifuge, drawn into a 100-$\mu$l syringe, and 3 $\mu$l sample was used for injection into each capillary. Capillaries were prerun at 80 V/cm for 5 min before each experiment. Diluted and deionized PCR samples were injected by inserting the capillary in a 5-$\mu$l sample volume held in an Eppendorf tube followed by electrokinetic injection (80 V/cm for 3 s). After injection, the sample tubes were replaced with tubes containing 0.8% HEC plus 1/2×TBE buffer. Electrophoresis was performed at 80 V/cm using 5-capillary arrays held at ambient temperature (22° C.). The low (80 V/cm) electrophoresis voltage was used to avoid undersampling of the bands with our current detection system which is limited to 1 Hz scan rates. When the experiments were complete, capillaries were flushed with water, then with methanol followed by drying. These coated capillaries could be refilled 20–25 times before the quality of the separations deteriorated. Methods for the further extension of the lifetime of capillary columns have been described.

PCR Amplification of THO1 loci. DNA was isolated from blood by using standard methods (Puers et al. (1993) Am. J. Hum. Genet. 53, 953–958). The human tyrosine hydroxylase locus HUMTHO1, chromosomal location 11p15.5, contains a polymorphic four base STR sequence (AATG) in intron 1[Puers, 1993, 953]. PCR-amplification of this polymorphic region produces allelic fragments designated "5" through "11", according to the number of AATG repeats; an additional allele designated "9.3" differs from allele 10 by a single base deletion. The primer sequences used for PCR are 5'-ATTCAAAGGGTATCTGGGCTCTGG-3' (THO1-A); SEQ ID No: 6 and 5'-GTGCGCTGAAAAGCTCCCGATTAT-3' (THO1-B); SEQ ID No: 7 (Edwards et al. (1991) Am. J. Hum. Genet. 49, 746–756). PCR amplifications were performed in 50 μl volumes by using 10 ng genomic DNA template, 0.5 μM of each primer, 5 units Taq DNA polymerase, 50 mM KCl, 1.5 mM $M_gCl_2$, 10 mM Tris-HCl at pH 8.3, and 200 μM dNTPs (final concentrations indicated). The PCR cycle protocol using a Perkin Elmer Cetus Model 480 was:

(1) melting at 95° C. for 5 min, (2) 30 cycles of 95° C. for 1 min, 58° C. for 1 min, and 72° C. for 1 min, (3) 72° C. for 7 min to complete extension. The PCR sample was then dialyzed for 30 min by pipeting 8–10 μl onto a 0.10 μm VCWP membrane filter (Millipore, Bedford, Mass.) which was floated on deionized water in a beaker held at 4° C. Dialysis was used to remove salts which can interfere with sample injection. Following dialysis, the samples were diluted with deionized water 100–1000 times (depending on product concentration) before electrokinetic injection. The amplifications with fluorescently labeled primers were also performed as described above. Initially four sets of fluorescent primers were used for PCR amplification and the mobility shifts of the products were evaluated with capillary electrophoresis. For these mobility shift experiments, 1–2 ng of unlabeled PCR product was reamplified by 20 PCR cycles using the appropriate fluorescent primers. THO1 types for all samples used in this study were independently determined by analysis on slab gels essentially as described by Puers et al., supra. Standard reference alleles were determined by sequence analysis.

I. Design and Synthesis of ET Primers.

Chemicals were purchased from Applied Biosystems (Foster City, Calif.). Oligodeoxynucleotides were synthesized by the phosphoramidite method on an Applied Biosystems 392 DNA synthesizer. Absorption spectra of the primers were measured on a Perkin-Elmer Lambda 6 UV-visible spectrophotometer and fluorescence emission spectra were taken on a Perkin-Elmer model MPF 44B spectrofluorimeter.

The structures of the four ET primers and a representative synthetic reaction are presented in Scheme 1. The THO1 primer (24-bases long) with the sequence 5'-ATTCAAAGGGTATCTGGGCTCTGG-3' (THO1-A); SEQ ID No: 6 and 5'-GTGGGCTGAAAAGCTCCCGATTAT-3' (THO1-B); SEQ ID No: 7 were synthesized with donor-acceptor fluorophore pairs separated by different distances. Each of the 24-mers contains a modified base (T*) introduced by the use of 5'-dimethoxytrityl-5-[N-(trifluoroacetyl-aminohexyl)-3-acr ylimido]-2'-deoxyuridine,3'-[(2-cyanoethyl)-(N,N-diisoprop yl)]-phosphoramidite (Amino-Modifier C6 dT, Glen Research, Sterling, Va.) (Structure 1), which has a protected primary amine linker arm. The donor dye was attached to the 5' end of the oligomer, and the acceptor dye was attached to the primary amine group on the modified base (T*). The ET primers are named using the abbreviation D-N-A, where D is the donor, A is the acceptor, and N is the number of bases between D and A. In the primers prepared, 5-carboxyfluorescein (FAM, F) is selected as a

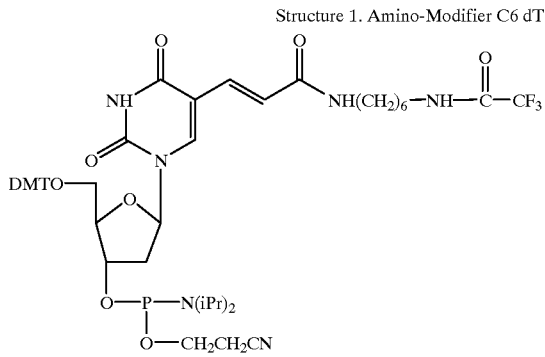

Structure 1. Amino-Modifier C6 dT common donor, and 6-carboxy-X-rhodamine (ROX, R) is selected as an acceptor. In the case of F10F and F14F, D=A=FAM. As a representative example, the structure of F6R is shown below (Structure 2).

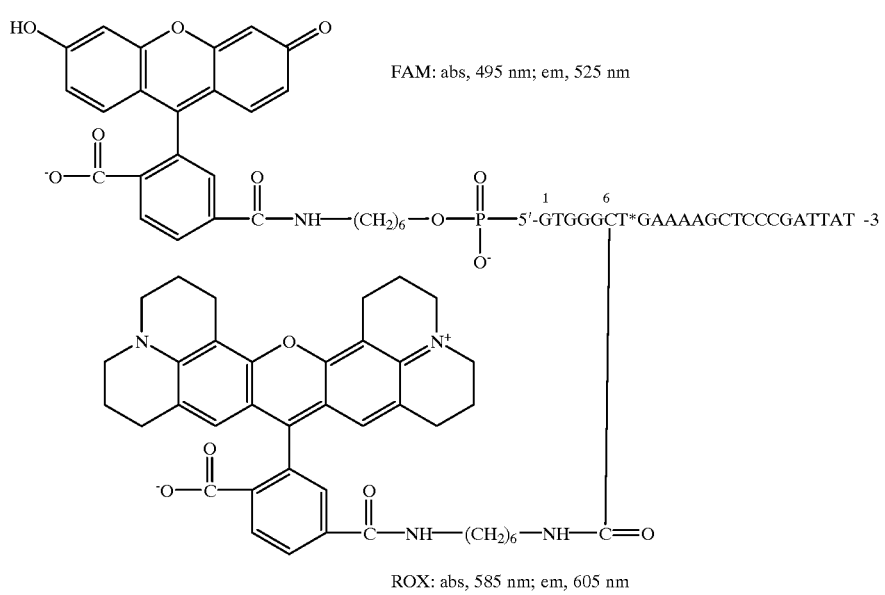

Structure 2. F6R (SEQ ID NO:9)

FAM: abs, 495 nm; em, 525 nm

ROX: abs, 585 nm; em, 605 nm

To prepare the ET primers, the donor FAM was introduced by using 6-FAM amidite in the last step of the oligonucleotide synthesis on a DNA synthesizer. After cleavage from the solid support and removal of the base protecting groups, the primers were evaporated to dryness under vacuum (0.5 mm Hg). To incorporate the acceptor dyes, 15–20 nmol of FAM-labeled T*-containing oligonucleotides in 40 μl 0.5 M $Na_2CO_3/NaHCO_3$ (pH 9.0) buffer were incubated overnight at room temperature with an approximately 150-fold excess of corresponding ROX or FAM N-hydroxy succinimidyl esters in 12 μl DMSO. Unreacted dye was removed by size exclusion chromatography on a Sephadex G-25 column (Pharmacia, Piscataway, N.J.). The ET primers were then purified by electrophoresis in a 20% polyacrylamide gel containing 6 M urea (40 cm×0.8 cm). The purified primers were recovered from the gel slices and desalted with Oligonucleotide Purification Cartridge (ABI). The single dye-labeled primers with the same sequence as that of the ET primers were prepared by the standard protocol using Aminolink 2 (ABI). The purity of the primers was shown to be >99% by polyacrylamide capillary gel electrophoresis. Primers were quantified by their 260 nm absorbances and then stored in 10 mM Tris-HCl, 1 mM EDTA (pH 8.0) at a final concentration of 10 pmol/μl for PCR reactions.

Figure 2:
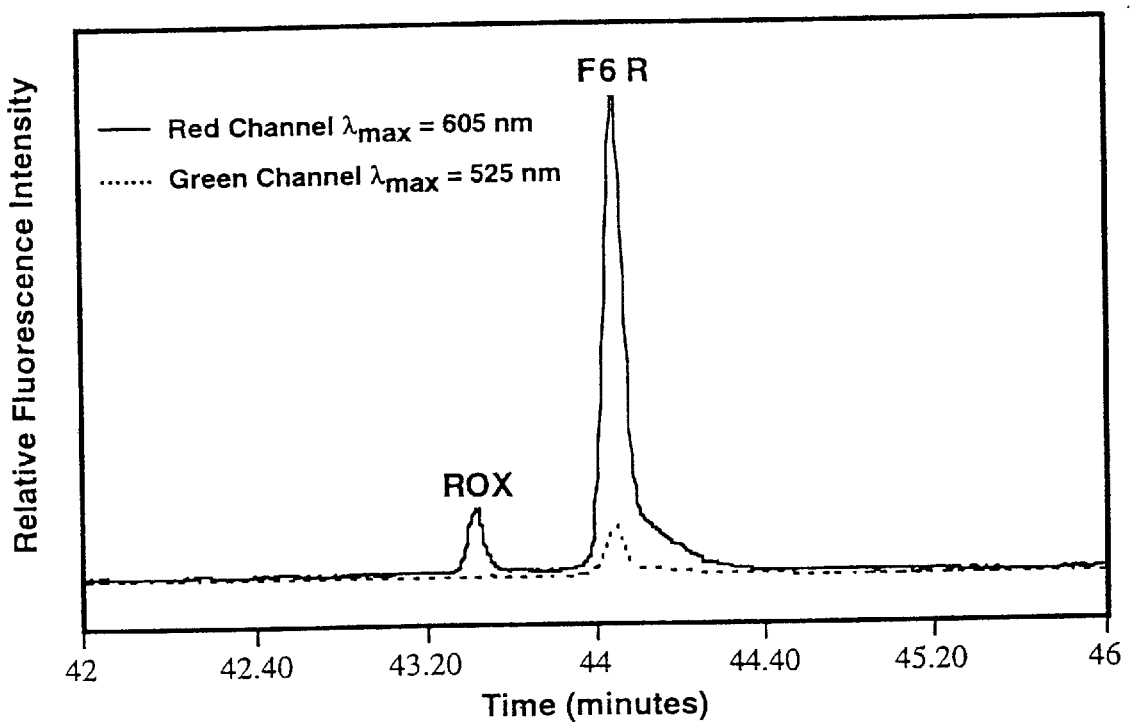
FIG. 2 shows the capillary electrophoresis (CE) electropherogram of primer F6R and ROX labeled primer. The two primers with the same sequence and same molar concentration were mixed together in 80% formamide and analyzed with a polyacrylamide gel filled capillary. The fluorescence signals were detected in the green ( - - - ) and red (_____) channels simultaneously with 488 nm excitation (argon laser). The fluorescence signal intensity of F6R is 8-fold higher than that of ROX labeled primer.

Four ET primers (F2R, F6R, F10F and F14F) were synthesized with the same donor at 5' end and different acceptors at different positions on the primer sequence. The spacing between the two chromophores is altered by varying the position of T* in the synthesis of each primer. It was found that the electrophoretic mobility of the ET primers depends on the spacing between the donor and acceptor. Within a range of distances determined by the number of intervening bases that allow good energy transfer, it is possible to adjust the electrophoretic mobility of the primers. The energy-transfer dye-labeled primers are advantageous for two-color fragment sizing because the 488-nm exciting light is optimally absorbed by the FAM chromophore in these primers followed by enhanced emission at the FAM wavelength in the case of F10F and F14F or very distinctively Stokes-shifted emission following energy transfer in the case of F2R and F6R. As representative examples, spectra of F14F and the energy transfer dye-labeled primer F6R are presented in FIG. 1. F14F exhibits strong absorption at ~488 nm and intense fluorescence emission with a maximum at 525 nm. F6R also exhibits intense absorption at 488 nm, but because of the FAM-to-ROX fluorescence energy transfer, the emission maximum is shifted out to ~600 nm and the energy transfer efficiency is over 90%. Substantial enhancement of the ET primer emission intensity compared to the single dye-labeled primer is observed. For example, FIG. 2 shows the fluorescence signal intensity comparison of the ET primer F6R with the corresponding single ROX-labeled primer in capillary electrophoresis. The two primers with the same sequence and same molar concentration were mixed together in 80% formamide and analyzed with a polyacrylamide gel filled capillary. The fluorescence intensity of F6R primer is 8-fold higher than and the ROX primer.

II. One-color Sizing of THO1 Alleles.

Figure 3:
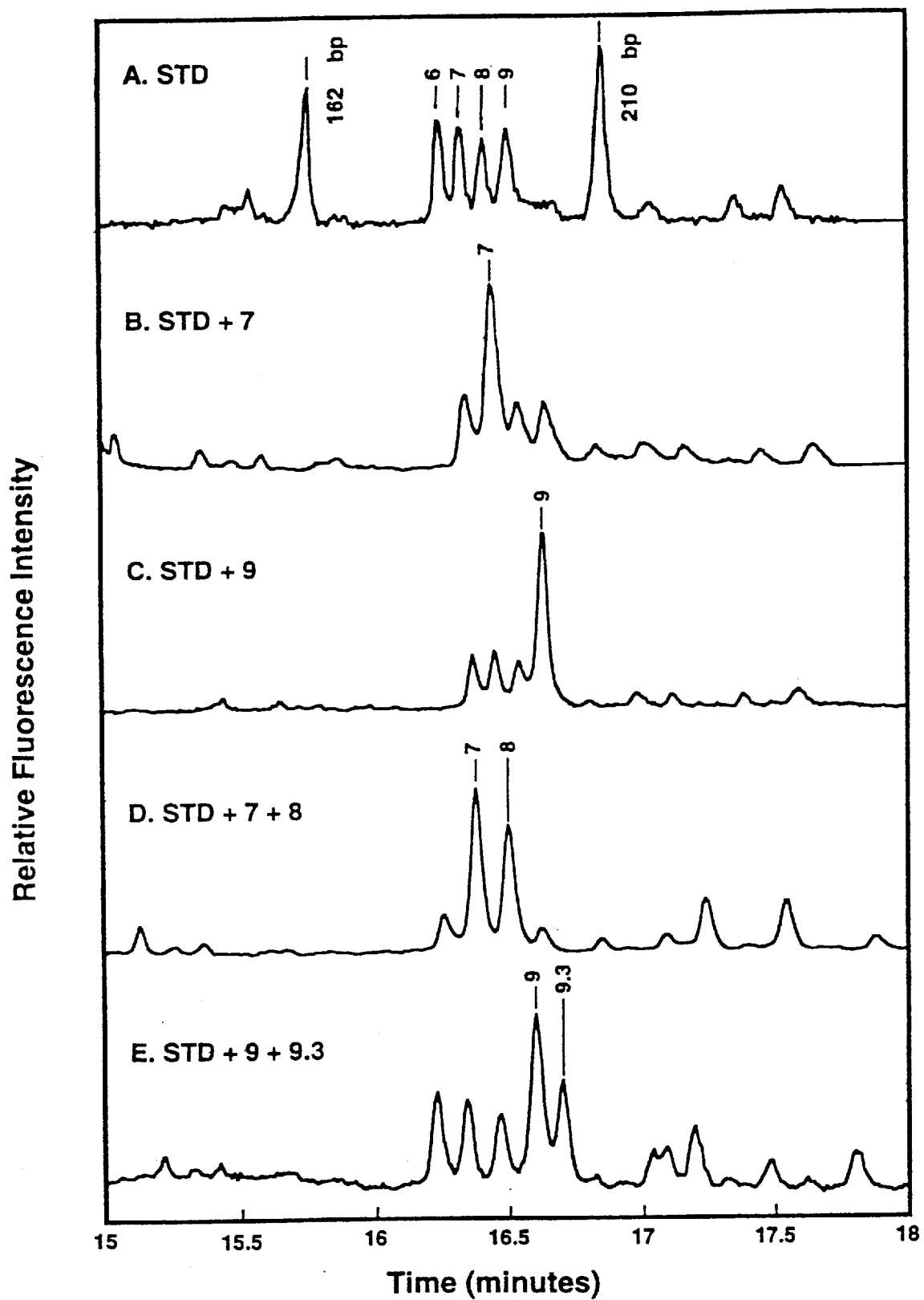
FIG. 3 shows the capillary electrophoresis electropherograms of (A) the THO1 standard ladder consisting of the 6, 7, 8, and 9 alleles which have been mixed and then coinjected with a φX-174 RF DNA-HincII digest. (B) Standard allelic ladder spiked with "unknown" allele 7. (C) Standard allelic ladder spiked with allele 9. (D) Standard allelic ladder spiked with alleles 7 and 8. (E) Standard allelic ladder spiked with alleles 9 and 9.3. These separations were run with 0.8% hydroxyethyl cellulose (HEC), 1/2×TBE and 1 µM thiazole orange in the running buffer and detected in the green channel. The additional weak peaks appearing at the detection times greater than ~17 min are due to heteroduplex formation.

FIG. 3 presents capillary array electrophoresis separations of the standard THO1 ladder that has been labeled on-column with the intercalating fluorophore, thiazole orange (TO) (Rye et al. (1991) Nucleic Acids Res. 19, 327–333). To form this standard ladder, two individual heterozygote samples containing alleles 6+9 and 7+8 were amplified and mixed. Trace A presents the electropherogram of the allelic ladder which was injected along with a φX-174 RF DNA-HincII restriction digest (Pharmacia, Piscataway, N.J.) as a control. The 4 alleles which are 4 bp apart are nearly baseline resolved with a separation time of less than 17 minutes. In trace B an "unknown" PCR-amplified sample is added to the allelic ladder and coinjected. The increased intensity of allele 7 identifies the unknown allele. Traces C, D and E in FIG. 3 similarly demonstrate the detection of samples containing alleles 9, 7+8, and 9+9.3. This work demonstrates the feasibility of producing the THO1 ladder for allelic typing with capillary array electrophoresis using nondenaturing HEC separation matrices. The use of a standard allelic ladder to perform accurate sizing has previously been reported. (Edwards et al. (1991) supra; Puers et al. (1993), supra) High-resolution separation of ds-DNA fragments on capillary columns has also been demonstrated by McCord et al. ((1993) J. Chromatogr. A, 652, 75–82 and (1993) J. Liq. Chromatogr. 16, 1963–1981). However, for one-color labeling of the allelic ladder and unknown to work reliably and precisely, it is necessary to have good control over the concentration of the DNA in the unknown samples. Alternatively, one could use a non-allelic ladder as the standard but there could be some loss of accuracy in the resulting interpolation.

III. Evaluation of Energy Transfer Primer Labeling.

For routine sizing experiments it is desirable to perform 2-color detection where the allelic standards are amplified with one fluorescent primer and the unknowns are amplified with a second fluorescent primer having a distinctive emission. Energy-transfer (ET) primers have the advantage of providing strong absorption at a common laser excitation wavelength (488 nm). Following the fluorescence energy transfer, the ET primers emit at a Stokes-shifted wavelength determined by the properties of the acceptor. Thus, the fluorescence emission of the ET primers is very intense, and the emission spectra of the different ET dye-labeled primers are distinctively Stokes-shifted. The ET primers can provide 8 times the signal strength compared to conventional single-dye labeled fluorescent primers as shown earlier. Furthermore, the mobility shift of DNA fragments generated with ET primers depends on the spacing between the dyes. Experiments were therefore performed to evaluate the mobility shift of the amplified fragments for all combinations of singly and doubly labeled targets.

Figure 4:
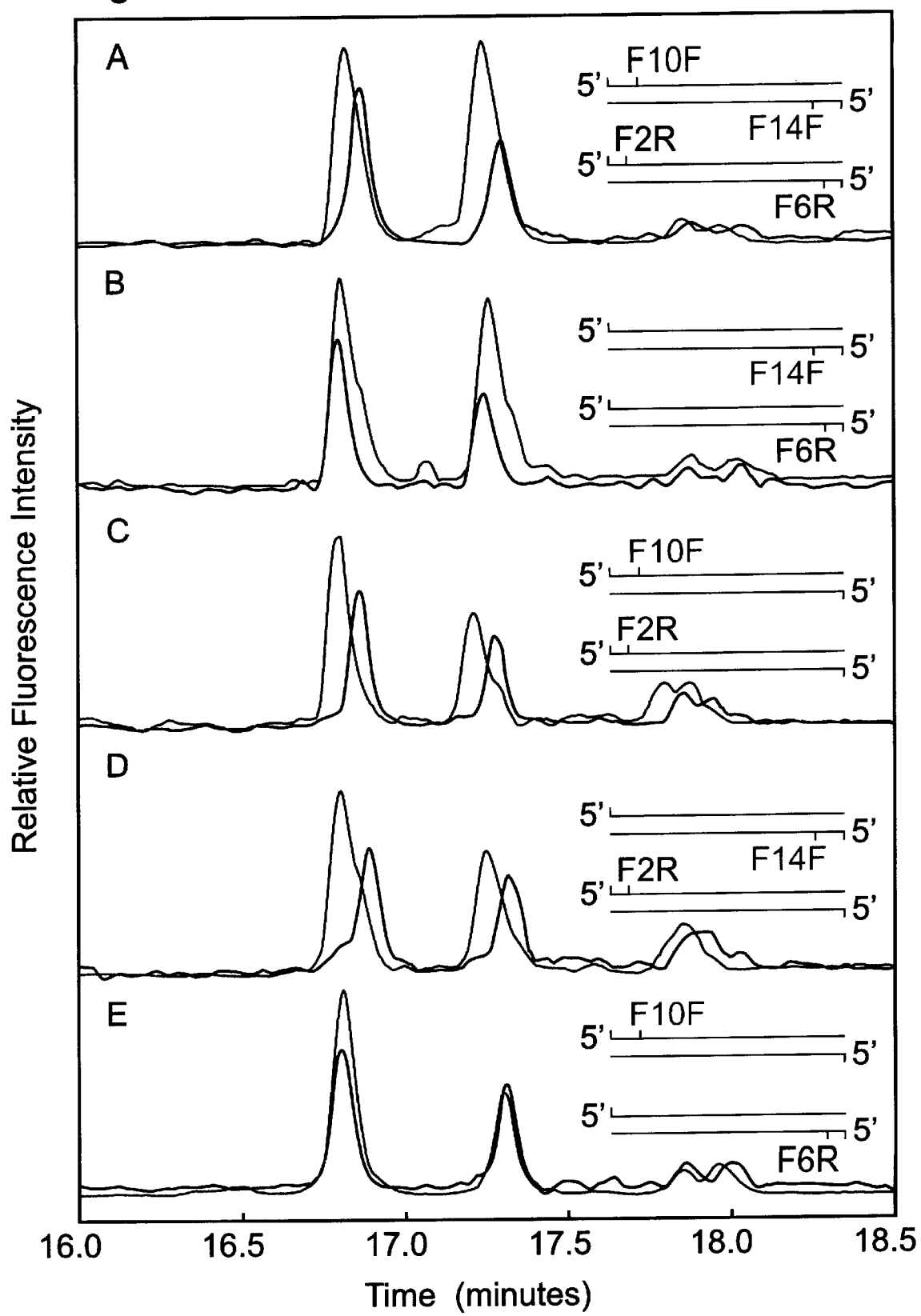
FIG. 4 shows the comparison of the mobility shift using five different methods for attaching energy-transfer coupled fluorophores to THO1 target alleles 6 and 9.3. The green line indicates the fluorescence intensity in the green channel and the red line indicates the intensity in the red channel. The structures of the primer sets used are indicated. Electrophoresis was performed using 0.8% HEC, 1/2×TBE and 1 µM 9-aminoacridine (9-AA) in the running buffer.

In trace A of FIG. 4, both strands of the amplified 6 and 9.3 targets have been labeled. In one case, the F10F primer is extended to form the (+) strand and the F14F primer is extended to form the (−) strand producing the green-emitting fragments. In the second case, the ET dye-labeled primer F2R is extended to produce the (+) strand and F6R is used to extend the (−) strand producing the red-emitting fragments. These fragments were mixed and electrophoresed on HEC-filled capillaries in the presence of 1 μM 9-aminoacridine (see below). The mobility shift between the green fragments and the red fragments in trace A was found to be ~2 bp. Thus, it was decided to evaluate amplifying with just one fluorescent primer per ds-DNA fragment to see if a particular combination of labels would reduce the mobility shift. Trace B in FIG. 4 shows that amplifying the (−) strand with the F14F primer or with the F6R primer generates fragments having almost no mobility shift (≦0.3 bp) between the green- and the red-labeled fragments. The two other labeling methods shown in traces C and D resulted in larger mobility shifts (2.4 bp). However, amplifying the (−) strand with F6R and the (+) strand with F10F also produced fragments having almost no mobility shift (trace E). The subsequent experiments were performed using the labeling method illustrated in trace B because these fragments are labeled on the same strand and can thus also be sized under denaturing conditions if necessary.

IV. Resolution Enhancement with 9-Aminoacridine.

To achieve satisfactory resolution of the THO1 allelic ladder, it was found that it is necessary to include an intercalating dye in the running buffer. Poor resolution is obtained when the allelic ladder (amplified with the F6R primer) is run in 0.8% HEC alone. The separation of the same ladder in 0.8% HEC plus 1 µM of the intercalating dye thiazole orange (TO) provided dramatically enhanced resolution. Electrophoresis in the presence of the intercalator ethidium bromide has also been shown to improve the electrophoretic resolution of ds-DNA.(Schwartz et al. (1991) J. Chromatogr. 559, 267–283; Guttman et al. (1991) Anal. Chem. 63, 2038–2042). Unfortunately, TO contributes to the signal in the green channel of our two-color detection system rendering it unsuitable for use in the desired two-color labeling scheme. It is thus necessary to use a non-fluorescent intercalator to improve the resolution. In electrophoretic separations of preformed dimeric dye : DNA complexes, Zhu et al.((1994) Anal. Chem. 66, 1941–1948) observed that the addition of the non-fluorescent dye 9-aminoacridine (9-AA) can be used to dramatically improve ds-DNA separation much like To and ethidium. Thus, the effect of 9-AA was evaluated. The separation is as good as that obtained in the presence of TO. The resolution improves significantly up to 1 µM 9-AA and is only slightly better at 5 µM. 9-AA concentrations above 50 µM were found to quench the fluorescence.

V. Two-color THO1 Sizing with Capillary Array Electrophoresis.

Figure 5:
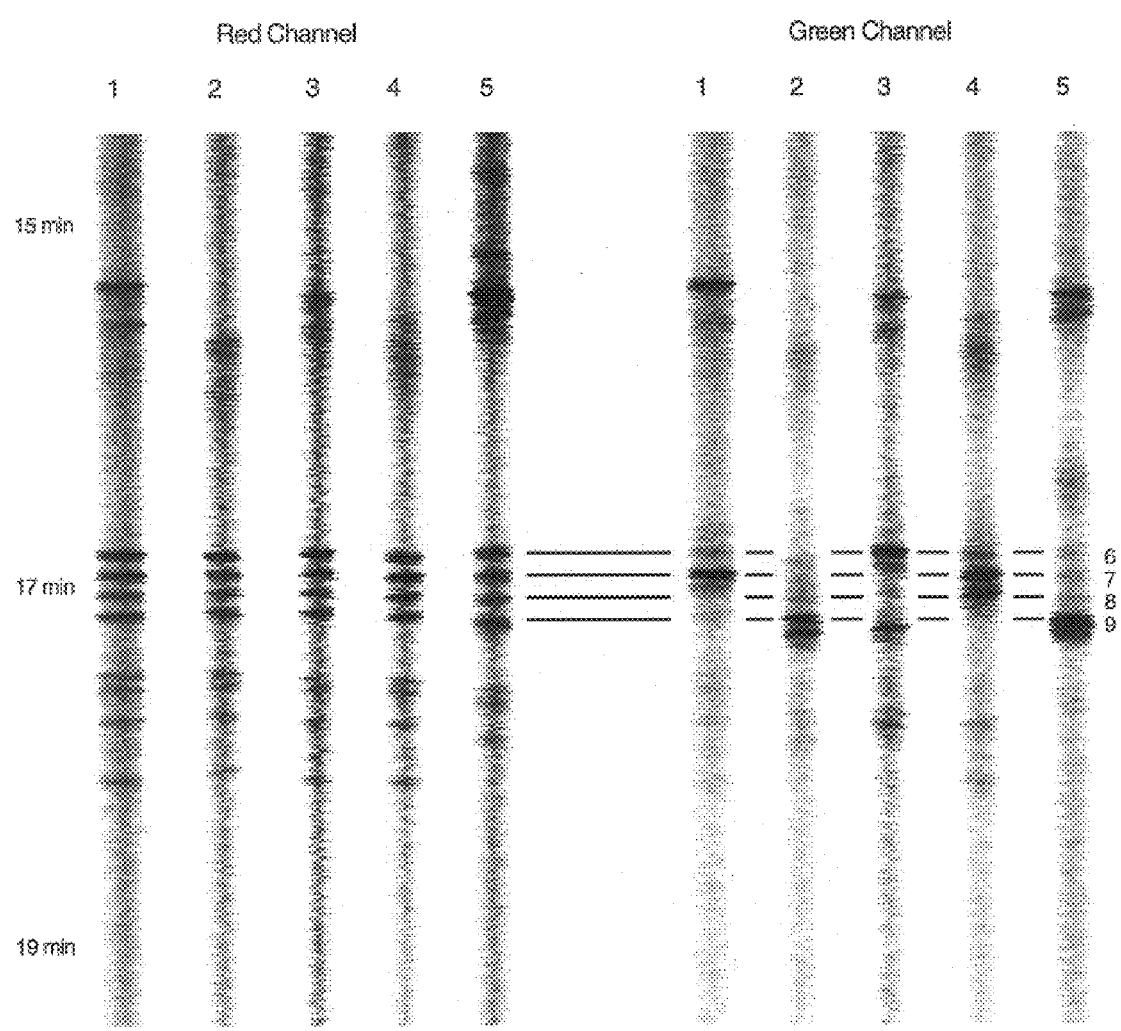
FIG. 5 shows the images of the fluorescence from a five capillary array separation of THO1 alleles. The left image presents the fluorescence signal as a function of time detected in the red (>590 nm) channel while the right image presents the fluorescence signal from the green ($\lambda$max=525 nm) channel. The standard THO1 allelic ladder (6+7+8+9) was amplified with the red emitting ET primer F6R and detected in the red channel; unknown alleles were amplified with the green emitting primer F14F and detected in the green channel. These images have been adjusted for the 1–2% capillary-to-capillary variance in mobility by shifting the time axes so that the allelic ladder is detected at the same time in all capillaries. This separation was performed with 0.8% HEC and 1 µM 9-AA in the running buffer at 80V/cm.
Figure 6:
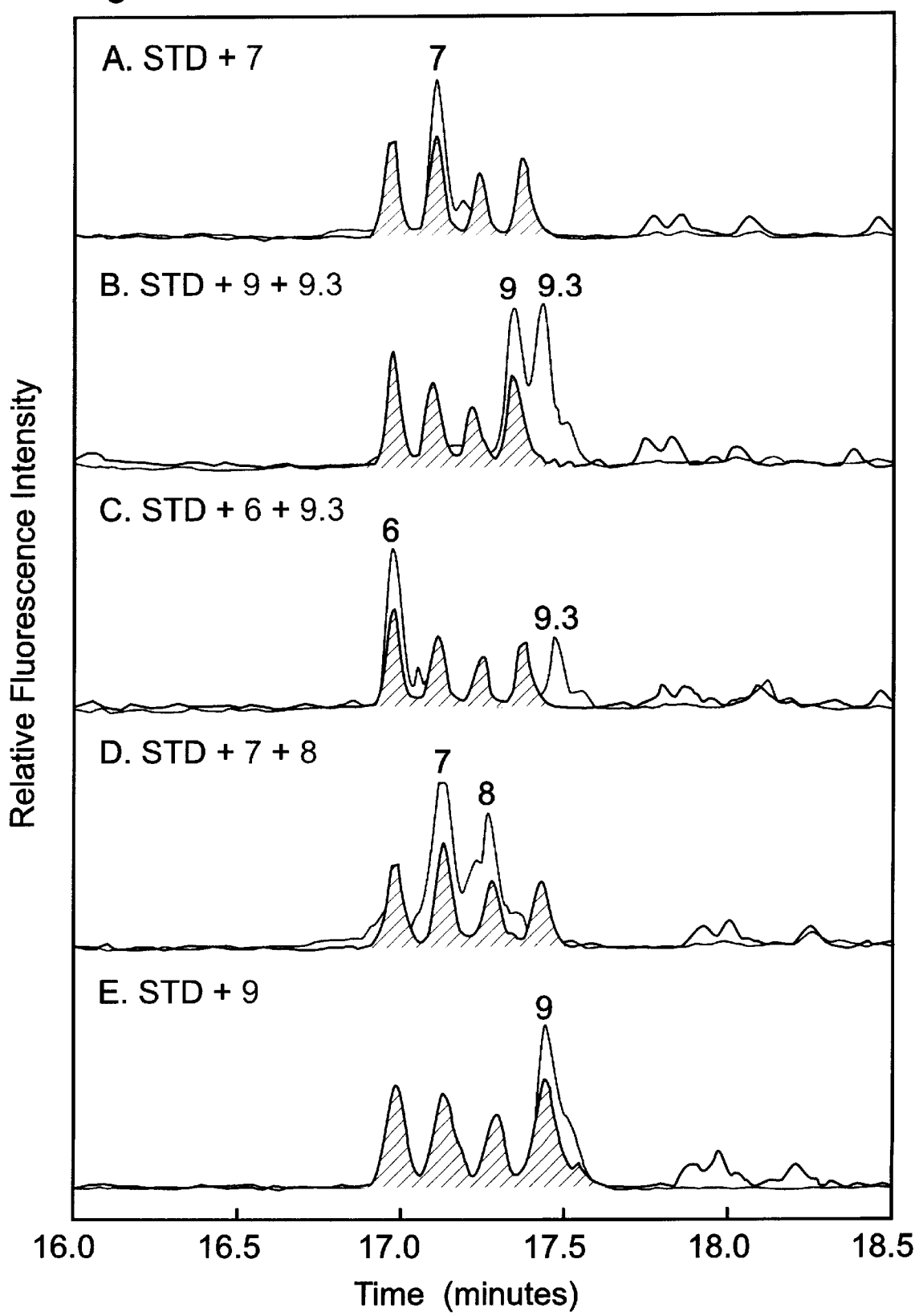
FIG. 6 shows the electropherograms of the THO1 fragment sizing separations presented in FIG. 5. The green signal is from the unknown alleles and the red signal is from the standard THO1 ladder. Traces A through E correspond to lanes 1–5 in FIG. 5.

FIG. 5 presents the results of a typical THO1 sizing experiment performed using two-color capillary array electrophoresis. The standard allelic ladder was amplified with F6R and detected in the red channel, while the unknown alleles were amplified with F14F and detected in the green channel. The signal detected as a function of time is presented as two images: the left image is the signal in the red channel and the right image is that detected in the green channel. The alleles appear at 17 minutes after injection. The signal in the red channel is predominantly from the red-labeled standard ladder and the expected 4 band patterns are seen in all capillaries. The unknown, amplified with the green emitting primer, is detected in the green channel. Allelic bands are identified as the intense green bands coinciding in mobility with allelic ladder bands in the red channel. To illustrate, the right image of FIG. 5 reveals intense green bands corresponding to allele 7 in lane 1, alleles 9+9.3 in lane 2, alleles 6+9.3 in lane 3, alleles 7+8 in lane 4, and allele 9 in lane 5. FIG. 6 presents electropherograms derived from the image in FIG. 5. Very clear discrimination is observed between the green-labeled fragments and the red-labeled fragments with almost no crosstalk between the green and red channels. In some cases, the amplification products of heterozygote samples contain heteroduplex bands that migrate behind the allelic ladder. Additional weak "noise" bands may represent non-templated base addition (Kimpton et al. (1993) PCR Methods and Applications 3, 13–22) known to occur with PCR amplification of THO1.

The accuracy and precision of allelic sizing using CAE was tested by performing multiple runs on 11 different samples. These results are summarized in Table 1.

TABLE 1

Statistical analysis of THO1 fragment sizing[1]

| Allele | Length (bp) | Determinations | Mean size[2] | S.D. (%)[3] |
|---|---|---|---|---|
| 6 | 183 | 6 | 183.1 | 0.61 (0.33) |
| 7 | 187 | 23 | 187.O | 0.41 (0.22) |
| 8 | 191 | 15 | 191.2 | 0.69 (0.36) |
| 9 | 195 | 1i | 195.4 | 0.60 (0.31) |
| 9.3 | 198 | 8. | 198.3 | 0.52 (0.26) |
| 10 | 199 | 6 | 199.O | 0.31 (0.15) |

[1]Eleven different amplified samples (7, 8), (6, 9.3), (9, 9.3), (6, 9), (7, 8), (8, 9), (7, 9.3), (7, 10), 6, 9.3), (7) and (9) were run 8, 2, 4, 3, 5, 2, 1, 6, 1, 3 and 2 times, respectively.
[2]Mean PCR product size as determined by linear regression using the allelic ladder as the sizing standard.
[3]Standard Deviation in terms of base pairs for the indicated number of determinations. The percent relative S.D. is given in parentheses.

Since a linear relationship exists between molecular weight and migration time in the region of interest, the allelic ladder was used with a linear regression analysis to size the unknown fragments. The calculated sizes of unknown alleles are compared to true sizes based on sequence analysis and verified by denaturing polyacrylamide gel electrophoresis. The average absolute difference of the determined allele sizes from the true allele sizes was 0.41 and over 70% of the determined values were within 0.5 bp of the true value. The reproducibility is excellent (relative standard deviation less than 0.4% for each allele) and there was no ambiguity in allele assignments. Two alleles, 9.3 and 10, which differ by a single base pair deletion can not be electrophoretically resolved when paired but can be correctly assigned when in combination with any other allele. It should however be possible to separate these two fragments on columns containing higher concentrations of HEC.

VI. Two-color Single Strand (ss) DNA Fragment Mobility Matching with ET Primers

The examples discussed above are for dsDNA fragments analysis. It was also found that the ssDNA fragments generated with ET primers with distinctive fluorescence emission can have substantially same mobility shifts on CE. The two primers are M13 (−40) F10F (SEQ ID NO:9) and F3R (SEQ ID NO:10), which have strong absorption at 488 nm and emitting fluorescence with maximum of 525 nm and 605 nm respectively. The primers were similarly prepared as discussed earlier and their structures are shown below:

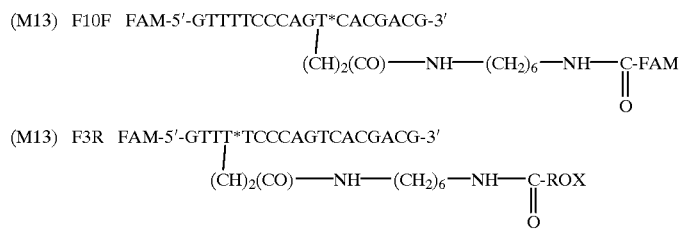

Figure 7:
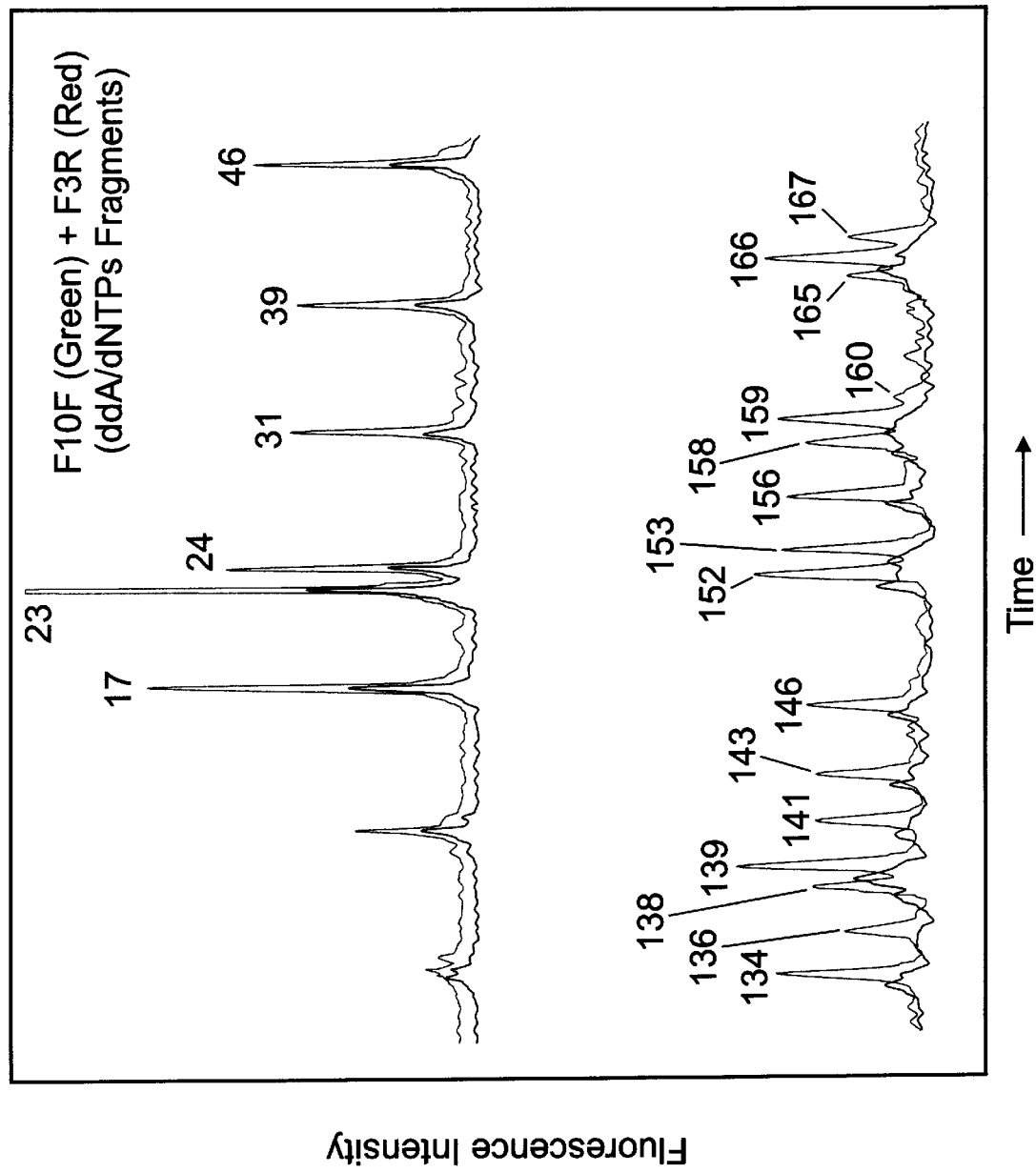
FIG. 7 shows the CE electropherogram of single strand (ss) DNA fragments generated with F10F and F3R primer and with ddATP/dNTPs. Green and red traces correspond to F10F and F3R DNA fragments which were detected in the green ($\lambda$max=525 nm) and red ($\lambda$>590 nm) channels respectively. ssDNA fragments were generated using Sequenase sequencing kit (USB/Amersham LIFE SCIENCE).

Fluorescent ddATP/dNTPs ssDNA fragments were produced with F10F and F3R primer and M13mp18 ssDNA template using Sequenase sequencing kit (USB/Amersham LIFE SCIENCE). The two sets of fragments were mixed together and analyzed on CE. Fluorescence signals were detected in the green (centered at 525 nm) and red (>590 nm) channels as described earlier. The CE electropherograms are shown in FIG. 7. The green peaks and the red peaks appear at almost the same time, indicating that the ssDNA fragments generated with F10F and F3R have substantially the same mobilities. This demonstrates that it is straightforward to use ET primers for ssDNA fragment analysis, such as fragment sizing with single base resolution using the appropriate sieving matrix for CE analysis.

It is evident from the above results, that one can tune related compositions, e.g. polynucleotides functionalized with 2 fluorophores to provide for different emission wavelengths and high emission quantum yields, while having substantially the same excitation-light absorbance and mobility. In this way, mixtures of compositions may be independently analyzed, where the different components may be differentially labeled with labels having differing fluorescence emission bands. Furthermore, the compositions can be readily prepared, can be used in a wide variety of contexts, and have good stability and enhanced fluorescent properties.

The advantages of the subject methodology and compositions are graphically exhibited with the detection of allelic short tandem repeats, where the repeating units will usually be under about 100 bp, usually under about 30 bp, and generally at least about 2 bp, frequently between 2 to 6 bp, and the number of repeating units will be at least about 3 repeat units. Fragments will usually be at least about 100 bp but can be 1000 bp and longer. There have been extensive reports on the use of STR for forensic identification. See, for example, Urquhart et al., BioTechniques (1995) 18:116–121; Fregeau and Fourney, BioTechniques (1993) 15:100–119; Kimpton et al., PCR Methods and Applications (1993) 3:13–22; McCord et al., J. of Chromatography (1993) A 652:75–82; and Mansfield, Human Molecular Genetics (1993) 2:43–50. The ET primers provide higher sensitivity and better color discrimination from that possible with conventional single dye-labeled fluorescent PCR primers. When used in conjunction with CAE on HEC capillary supports containing an intercalator in the buffer, the HEC solutions provide high speed separations on columns that can be easily refilled and rerun. The amplification of single tandem repeat targets with different fragment lengths in the 100–500 bp size range plus the use of up to 4 different ET primers provides an additional increase in the speed and throughput of single tandem repeat typing.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying and distinguishing at least two different nucleic acids produced using a nucleic acid polymerase comprising:

a) producing said at least two different nucleic acids using said nucleic acid polymerase such that at least one nucleic acid is covalently bonded to a first fluorescent energy-transfer label, and at least one nucleic acid is covalently bonded to a second fluorescent energy-transfer label,
wherein said first fluorescent energy-transfer label comprises a first fluorescent donor and a first fluorescent acceptor covalently bonded to a first backbone chain at specific locations thereon with energy transfer from said first donor to said first acceptor, and said second fluorescent energy-transfer label comprises a second fluorescent donor and a second fluorescent acceptor covalently bonded to a second backbone chain at specific locations thereon with energy transfer from said second donor to said second acceptor,
provided that the absorption wavelengths of said first donor and said second donor are substantially the same, and said first acceptor and said second acceptor each have different emission wavelengths;
b) separating said at least two different nucleic acids; and
c) identifying and distinguishing said at least two different nucleic acids separated in said step (b) by irradiating with light absorbed by said first donor and second donor and detecting light emission from said first acceptor and said second acceptor.

2. The method of claim 1, wherein said first donor and said second donor are the same.

3. The method of claim 2, wherein said first backbone and said second backbone are different.

4. The method of claim 2, wherein said first donor and said second donor each absorb light in the wavelength range of 350–800 nm, and said first acceptor and said second acceptor each emit light in the wavelength range of 450–1000 nm.

5. The method of claims 1–3 or 4, wherein step (b) uses a single lane or a single capillary to separate said at least two different nucleic acids by electrophoresis.

6. The method of claims 1–3 or 4, wherein said first and second backbone chains each comprise a bi-functional group.

7. The method of claims 1–3 or 4, wherein said first and second fluorescent energy transfer labels are each initially present on a primer.

8. A method of identifying and distinguishing at least four different nucleic acids produced using a nucleic acid polymerase comprising:
a) producing said at least four different nucleic acids using said nucleic acid polymerase such that at least one nucleic acid is covalently bonded to a first fluorescent energy-transfer label, at least one nucleic acid is covalently bonded to a second fluorescent energy-transfer label, at least one nucleic acid is covalently bonded to a third fluorescent energy-transfer label, and at least one nucleic acid is covalently bonded to a fourth fluorescent energy-transfer label,
wherein said first fluorescent energy-transfer label comprises a first fluorescent donor and a first fluorescent acceptor covalently bonded to a first backbone chain at specific locations thereon with energy transfer from said first donor to said first acceptor, said second fluorescent energy-transfer label comprises a second fluorescent donor and a second fluorescent acceptor covalently bonded to a second backbone chain at specific locations thereon with energy transfer from said second donor to said second acceptor, said third fluorescent energy-transfer label comprises a third fluorescent donor and a third fluorescent acceptor covalently bonded to a third backbone chain at specific locations thereon with energy transfer from said third donor to said third acceptor, and said fourth fluorescent energy-transfer label comprises a fourth fluorescent donor and a fourth fluorescent acceptor covalently bonded to a fourth backbone chain at specific locations thereon with energy transfer from said fourth donor to said fourth acceptor,
provided that the absorption wavelengths of said first donor, said second donor, said third donor, and said fourth donor, are substantially the same; and said first acceptor, said second acceptor, said third acceptor, and said fourth acceptor, each have different emission wavelengths;
b) separating said at least four different nucleic acids; and
c) identifying and distinguishing said at least four different nucleic acids separated in said step (b) by irradiating with light absorbed by said first donor, said second donor, said third donor, and said fourth donor; and detecting light emission from said first acceptor, said second acceptor, said third acceptor, and said fourth acceptor.

9. The method of claim 8, wherein said first donor, said second donor, said third donor, and said fourth donor are the same.

10. The method of claim 9, wherein said first backbone, said second backbone, said third backbone, and said fourth backbone are different.

11. The method of claim 10, wherein said first donor, said second donor, said third donor, and said fourth donor each absorb light in the wavelength range of 350–800 nm; and said first acceptor, said second acceptor, said third acceptor, and said fourth acceptor each emit light in the wavelength range of 450–1000 nm.

12. The method of claims 8–10 or 11, wherein step (b) uses a single lane or a single capillary to separate said at least four different nucleic acids by electrophoresis.

13. The method of claims 8–10 or 11, wherein said first, second, third and fourth backbone chains each comprise a bi-functional group.

14. The method of claims 8–10 or 11, wherein said first, second, third and fourth fluorescent energy-transfer labels are each initially present on a primer.

15. A method of identifying and distinguishing different deoxyribonucleic acids produced in chain termination sequencing reactions comprising:
a) producing a first, a second, a third, and a fourth set of different size deoxyribonucleic acids complementary to a deoxyribonucleic acid template using a nucleic acid polymerase wherein,
said first set comprises different size deoxyribonucleic acids covalently bonded to a first fluorescent energy-transfer label and terminates with a chain terminator comprising a nitrogenous base complementary to adenine,
said second set comprises different size deoxyribonucleic acids covalently bonded to a second fluorescent energy-transfer label and terminates with a chain terminator comprising a nitrogenous base complementary to guanine,
said third set comprises different size deoxyribonucleic acids covalently bonded to a third fluorescent energy-transfer label and terminates with a chain terminator comprising a nitrogenous base complementary to thymine, and
said fourth set comprises different size deoxyribonucleic acids covalently bonded to a fourth fluorescent energy-transfer label and terminates with a chain terminator comprising a nitrogenous base complementary to cytosine, provided that said first fluorescent energy-transfer label comprises a first fluorescent donor and a first fluorescent acceptor covalently bonded to a first backbone chain at specific locations thereon with energy transfer from said first donor to said first acceptor, said second fluorescent energy-transfer label comprises a second fluorescent donor and a second fluorescent acceptor covalently bonded to a second backbone chain at specific locations thereon with energy transfer from said second donor to said second acceptor, said third fluorescent energy-transfer label comprises a third fluorescent donor and a third fluorescent acceptor covalently bonded to a third backbone chain at specific locations thereon with energy transfer from said third donor to said third acceptor, and said fourth fluorescent energy-transfer label comprises a fourth fluorescent donor and a fourth fluorescent acceptor covalently bonded to a fourth backbone chain at specific locations thereon with energy transfer from said fourth donor to said fourth acceptor, further provided that the absorption wavelengths of said first donor, said second donor, said third donor, and said fourth donor are substantially the same, and said first acceptor, said second acceptor, said third acceptor, and said fourth acceptor, each have different emission wavelengths;

b) separating said different size deoxyribonucleic acids complementary to said deoxyribonucleic acid template produced in said step (a); and c) identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

16. The method of claim 15, wherein said first label, said second label, said third label, and said fourth label each have substantially the same mobility under conditions used in said step (b).

17. The method of claim 15, wherein said first label, said second label, said third label, and said fourth label have a mobility differing by not more than 10% under conditions used in said step (b).

18. The method of claim 15, wherein said first label, said second label, said third label, and said fourth label each have a mobility differing by not more than 5% under conditions used in step (b).

19. The method of claim 16, wherein said first label, said second label, said third label, and said fourth label have the same mobility under conditions used in step (b).

20. (new) The method of claim 16, wherein said first donor, said second donor, said third donor, and said fourth donor are the same.

21. The method of claim 20, wherein said first backbone, said second backbone, said third backbone, and said fourth backbone are different.

22. The method of claim 21, wherein said first donor, said second donor, said third donor, and said fourth donor each absorb light in the wavelength range of 350–800 nm; and said first acceptor, said second acceptor, said third acceptor, and said fourth acceptor each emit light in the wavelength range of 450–1000 nm.

23. The method of claims 15–20 or 21, wherein step (b) uses a single lane or a single capillary to separate said different size nucleic acids complementary to said deoxyribonucleic acid template by electrophoresis.

24. The method of claims 15–20 or 21, wherein said first, second, third and fourth backbone chains each comprise a bi-functional group.

25. The method of claims 15–20 or 21, wherein said first, second, third and fourth fluorescent energy-transfer labels are each initially present on a primer.

26. A method of determining the sequence of a deoxyribonucleic acid template comprising:

a) producing a first, a second, a third, and a fourth set of different size deoxyribonucleic acids complementary to a deoxyribonucleic acid template using a nucleic acid polymerase wherein:

said first set comprises different size deoxyribonucleic acids covalently bonded to a first fluorescent energy-transfer label and terminates with a chain terminator comprising a nitrogenous base complementary to adenine, said second set comprises different size deoxyribonucleic acids covalently bonded to a second fluorescent energy-transfer label and terminates with a chain terminator comprising a nitrogenous base complementary to guanine, said third set comprises different size deoxyribonucleic acids covalently bonded to a third fluorescent energy-transfer label and terminates with a chain terminator comprising a nitrogenous base complementary to cytosine, and said fourth set comprises different size deoxyribonucleic acids covalently bonded to a fourth fluorescent energy-transfer label and terminates with a chain terminator comprising a nitrogenous base complementary to thymine, provided that said first fluorescent energy-transfer label comprises a first fluorescent donor and a first fluorescent acceptor covalently bonded to a first backbone chain at specific locations thereon with energy transfer from said first donor to said first acceptor, said second fluorescent energy-transfer label comprises a second fluorescent donor and a second fluorescent acceptor covalently bonded to a second backbone chain at specific locations thereon with energy transfer from said second donor to said second acceptor, said third fluorescent energy-transfer label comprises a third fluorescent donor and a third fluorescent acceptor covalently bonded to a third backbone chain at specific locations thereon with energy transfer from said third donor to said third acceptor, and said fourth fluorescent energy-transfer label comprises a fourth fluorescent donor and a fourth fluorescent acceptor covalently bonded to a fourth backbone chain at specific locations thereon with energy transfer from said fourth donor to said fourth acceptor, further provided that the absorption wavelengths of said first donor, said second donor, said third donor, and said fourth donor are substantially the same, and said first acceptor, said second acceptor, said third acceptor, and said fourth acceptor each have different emission wavelengths;

b) separating said different size deoxyribonucleic acids complementary to said deoxyribonucleic acid template produced in said step (a), wherein the mobilities of said first fluorescent energy-transfer label, said second fluorescent energy-transfer label, said third fluorescent energy-transfer label, and said fourth fluorescent energy-transfer label are each substantially the same; and c) determining said sequence of said template by identifying and distinguishing said different size deoxyribonucleic acids complementary to said deoxyribonucleic acid template separated in said step (b) by irradiating with light absorbed by said first donor, said second donor, said third donor, and said fourth donor; and detecting light emission from said first acceptor, said second acceptor, said third acceptor, and said fourth acceptor.

27. The method of claim 26, wherein said first label, said second label, said third label, and said fourth label each have the same mobility under conditions used in step (b).

28. The method of claim 26, wherein said first label, said second label, said third label, and said fourth label have mobilities differing by not more than 10% under conditions used in step (b).

29. The method of claim 26, wherein said first label, said second label, said third label, and said fourth label have mobilities differing by not more than 5% under conditions used in said step (b).

30. The method of claim 27, wherein said first donor, said second donor, said third donor, and said fourth donor are the same.

31. The method of claim 30, wherein said first backbone, said second backbone, said third backbone, and said fourth backbone are different.

32. The method of claim 30, wherein said first donor, said second donor, said third donor, and said fourth donor each absorb light in the wavelength range of 350–800 nm; and said first acceptor, said second acceptor, said third acceptor, and said fourth acceptor each emit light in the wavelength range of 450–1000 nm.

33. The method of claims 26–31 or 32 wherein step (b) uses a single lane or a single capillary to separate said different size nucleic acids by electrophoresis.

34. The method of claims 26–31 or 32 wherein said first, second, third and fourth backbone chains each comprise a bi-functional group.

35. The method of claims 26–31 or 32 wherein said first, second, third and fourth fluorescent energy-transfer labels are each initially present on a primer.

36. An improved method of identifying and distinguishing nucleic acid fragments produced by sequencing reactions and separated by their mobility in a separation system, the improvement comprising the use of a first, a second, a third, and a fourth fluorescent energy-transfer label, having substantially the same mobility in said separation system, to covalently label said fragments, wherein said first fluorescent energy-transfer label comprises a first fluorescent donor and a first fluorescent acceptor covalently bonded to a first backbone chain at specific locations thereon with energy transfer from said first donor to said first acceptor, said second fluorescent energy-transfer label comprises a second fluorescent donor and a second fluorescent acceptor covalently bonded to a second backbone chain at specific locations thereon with energy transfer from said second donor to said second acceptor, said third fluorescent energy-transfer label comprises a third fluorescent donor and a third fluorescent acceptor covalently bonded to a third backbone chain at specific locations thereon with energy transfer from said third donor to said third acceptor, and said fourth fluorescent energy-transfer label comprises a fourth fluorescent donor and a fourth fluorescent acceptor covalently bonded to a fourth backbone chain at specific locations thereon with energy transfer from said fourth donor to said fourth acceptor.

37. The method of claim 36, wherein first label, said second label, said third label, and said fourth label have mobilities differing by not more than 10% in said separation system.

38. The method of claim 36, wherein said first label, said second label, said third label, and said fourth label have mobilities differing by not more than 5% in said separation system.

39. The method of claim 36, wherein said first donor, said second donor, said third donor, and said fourth donor are the same.

40. The method of claim 36, wherein said first backbone, said second backbone, said third backbone, and said fourth backbone are different.

41. The method of claim 36, wherein said first donor, said second donor, said third donor, and said fourth donor each absorb light in the wavelength range of 350–800 nm; and said first acceptor, said second acceptor, said third acceptor, and said fourth acceptor each emit light in the wavelength range of 450–1000 nm.

42. The method of claims 36–40 or 41, wherein step (b) uses a single lane or a single capillary to separate said different size nucleic acids by electrophoresis.

43. The method of claims 36–40 or 41, wherein said first, second, third and fourth backbone chains each comprise a bi-functional group.

44. The method of claims 36–40 or 41, wherein said first, second, third and fourth fluorescent energy-transfer labels are each initially present on a primer.

45. A method for determining the nucleotide base sequence of a deoxyribonucleic acid comprising, a) contacting said deoxyribonucleic acid with at least four different dNTPs, a primer, and at least one ddNTP in the presence of a label, under conditions in which said primer is extended to form extension products by addition of at least one dNTP wherein a ddNTP is covalently bonded to said primer, or to said at least one dNTP covalently bonded to said primer, and wherein said label is a fluorescent energy-transfer label, wherein said extension products are also covalently bonded to said label, and further wherein a different said label is caused to be covalently bonded with primer extension products comprising different ddNTPs such that each said label can be used to identify a primer extension reaction produced comprising a specific ddNTP, provided that each said different label comprises a first, a second, a third, and a fourth fluorescent energy-transfer label, wherein said first fluorescent energy-transfer label comprises a first fluorescent donor and a first fluorescent acceptor covalently bonded to a first backbone chain at specific locations thereon with energy transfer from said first donor to said first acceptor, said second fluorescent energy-transfer label comprises a second fluorescent donor and a second fluorescent acceptor covalently bonded to a second backbone chain at specific locations thereon with energy transfer from said second donor to said second acceptor, said third fluorescent energy-transfer label comprises a third fluorescent donor and a third fluorescent acceptor covalently bonded to a third backbone chain at specific locations thereon with energy transfer from said third donor to said third acceptor, and said fourth fluorescent energy-transfer label comprises a fourth fluorescent donor and a fourth fluorescent acceptor covalently bonded to a fourth backbone chain at specific locations thereon with energy transfer from said fourth donor to said fourth acceptor;

b) separating said extension products produced in said step (a), wherein the mobility of each said different label is substantially the same; and c) identifying and distinguishing said extension products separated in said step (b) by irradiating with light absorbed by said first donor, said second donor, said third donor, and said fourth donor; and detecting light emission from said first acceptor, said second acceptor, said third acceptor, and said fourth acceptor.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: 1
       (D) OTHER INFORMATION: /mod_base= OTHER
           /note= "N = adenosine modified by 5-carboxyfluorescein
           through an aminohexyl linker"

(ix) FEATURE:
       (A) NAME/KEY: modified_base
       (B) LOCATION: 11
       (D) OTHER INFORMATION: /mod_base= OTHER
           /note= "N = thymidine modified by 5-carboxyfluorescein
           through an aminohexylacrylimido linker"

(xi) SEQUENCE DESCRIPTION: SEQ ID NO:1:

NTTCAAAGGG NATCTGGGCT CTGG                                                 24

(2) INFORMATION FOR SEQ ID NO:2:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by 5-carboxyfluorescein
                through an aminohexyl linker"

(ix) FEATURE:
            (A) NAME/KEY: modified_base
            (B) LOCATION: 15
            (D) OTHER INFORMATION: /mod_base= OTHER
                /note= "N = thymidine modified by 5-carboxyfluorescein
                through an aminohexylacrylimido linker"

(xi) SEQUENCE DESCRIPTION: SEQ ID NO:2:

NTGGGCTGAA AAGCNCCCGA TTAT                                                24

(2) INFORMATION FOR SEQ ID NO:3:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = adenosine modified by 5-carboxyfluorescein
                through an aminohexyl linker"

(ix) FEATURE:
            (A) NAME/KEY: modified_base
            (B) LOCATION: 3
            (D) OTHER INFORMATION: /mod_base= OTHER
                /note= "N = thymidine modified by 6-carboxy-X-rhodamine
                through an aminohexylacrylimido linker"

(xi) SEQUENCE DESCRIPTION: SEQ ID NO:3:

NTNCAAAGGG TATCTGGGCT CTGG                                                24

(2) INFORMATION FOR SEQ ID NO:4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = guanosine modified by 6-carboxyfluorescein
                through an aminohexyl linker"

(ix) FEATURE:
            (A) NAME/KEY: modified_base
            (B) LOCATION: 7
            (D) OTHER INFORMATION: /mod_base= OTHER
                /note= "N = thymidine modified by 6-carboxy-X-rhodamine
                through an aminohexylacrylimido linker"

(xi) SEQUENCE DESCRIPTION: SEQ ID NO:4:

NTGGGCNGAA AAGCTCCCGA TTAT                                    24

(2) INFORMATION FOR SEQ ID NO:5:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 1
      (D) OTHER INFORMATION: /mod_base= OTHER
        /note= "N = guanosine modified by 5-carboxyfluorescein
        through an aminohexyl linker"

(ix) FEATURE:
      (A) NAME/KEY: modified_base
      (B) LOCATION: 7
      (D) OTHER INFORMATION: /mod_base= OTHER
        /note= "N = thymidine modified by an aminohexylacrylimide
        linker"

(xi) SEQUENCE DESCRIPTION: SEQ ID NO:5:

NTGGGCNGAA AAGCTCCCGA TTAT                                    24

(2) INFORMATION FOR SEQ ID NO:6:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:6:

ATTCAAAGGG TATCTGGGGC TCTGG                                   25

(2) INFORMATION FOR SEQ ID NO:7:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:7:

GTGGGCTGAA AAGCTCCCGA TTAT                                    24

(2) INFORMATION FOR SEQ ID NO:8:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 1
      (D) OTHER INFORMATION: /mod_base= OTHER

```
            /note= "N = guanosine modified by 5-carboxyfluorescein
            through an aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by
            N,N,N',N'-tetramethyl-6-carboxyrhodamine through an
            aminohexylimido linker"

(xi) SEQUENCE DESCRIPTION: SEQ ID NO:8:

NTTNTCCCAG TC                                                            12

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by 5-carboxyfluorescein
            through an aminohexyl linker"

(ix) FEATURE:
        (A) NAME/KEY: modified_base
        (B) LOCATION: 11
        (D) OTHER INFORMATION: /mod_base= OTHER
            /note= "N = thymidine modified by 5-carboxyfluorescein
            through an aminohexylacrylimido linker"

(xi) SEQUENCE DESCRIPTION: SEQ ID NO:9:

NTTTTCCCAG NCACGACG                                                      18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = guanosine modified by 5-carboxyfluorescein
            through an aminohexyl linker"

(ix) FEATURE:
        (A) NAME/KEY: modified_base
        (B) LOCATION: 4
        (D) OTHER INFORMATION: /mod_base= OTHER
            /note= "N = thymidine modified by 6-carboxy-X-rhodamine
            through an aminohexylacrylimido linker"

(xi) SEQUENCE DESCRIPTION: SEQ ID NO:10:

NTTNTCCCAG TCACGACG                                                      18
```